United States Patent [19]

Seidoh et al.

[11] Patent Number: 5,343,770
[45] Date of Patent: Sep. 6, 1994

[54] AUTOMATIC SAMPLE INTRODUCER FOR ANALYZER

[75] Inventors: Akinori Seidoh; Youzo Morita; Hiroaki Matsuhisa, all of Kyoto, Japan

[73] Assignee: Shimadzu Corporation, Kyoto, Japan

[21] Appl. No.: 737,061

[22] Filed: Jul. 29, 1991

[30] Foreign Application Priority Data

Jul. 27, 1990 [JP] Japan ............................ 2-80324[U]
Jul. 27, 1990 [JP] Japan ............................ 2-199863

[51] Int. Cl.⁵ .......................................... G01N 35/06
[52] U.S. Cl. ......................... 73/864.22; 73/864.21; 422/64
[58] Field of Search .......... 73/864.22, 864.21, 864.17, 73/863.32; 422/64

[56] References Cited

U.S. PATENT DOCUMENTS

| | | | |
|---|---|---|---|
| 3,192,968 | 7/1965 | Baruch et al. | 73/864.24 X |
| 3,282,651 | 11/1966 | Ferrari et al. | 73/863.32 |
| 3,536,449 | 10/1970 | Astle | 73/863.32 X |
| 3,687,632 | 8/1972 | Natelson | 73/864.25 |
| 3,912,456 | 10/1975 | Young | 73/864.25 X |
| 4,341,736 | 7/1982 | Orbal et al. | 73/864.25 X |
| 4,841,786 | 6/1989 | Schulz | 73/864.25 |
| 5,183,638 | 2/1993 | Wakatake | 422/67 X |

FOREIGN PATENT DOCUMENTS 2044954 10/1980 United Kingdom ............ 73/863.32

*Primary Examiner*—Tom Noland
*Attorney, Agent, or Firm*—William L. Klima

[57] ABSTRACT

A sampling needle and a ventilation pretreatment needle for sparging out a gas containing no carbon component are mounted on the same arm mechanism to be simultaneously driven. The sampling needle is adapted to introduce samples as well as to distributively inject acid into sample containers. The ventilation pretreatment needle is adapted to stir samples during sampling as well as to pretreat next samples during analysis.

17 Claims, 7 Drawing Sheets

AUTOMATIC SAMPLE INTRODUCER FOR ANALYZER

BACKGROUND OF THE INVENTION

1. Field of the Invention

The present invention relates to a sample introducer, which is suitable for automatically introducing samples into an analyzer such as a total organic carbon (TOC) analyzer.

2. Description of the Background Art

A certain type of a TOC analyzer is applied not only to total carbon (TC) measurement but also to inorganic carbon (IC) measurement, total organic carbon (TOC) measurement, non-purgeable organic carbon (NPOC) measurement, and the like. A sample introducer is provided with a sampling needle for sucking sample solutions as well as a sparging needle for sparging (i.e. blowing a gas into a sample) a gas containing no $CO_2$ gas into the samples before or during the suction for homogenizing the samples or for sparging the gas into previously acidified sample solutions for removing IC before measuring NPOC. Such needles are individually driven by different driving mechanisms, to be inserted in the sample containers.

In order to perform NPOC measurement, it is necessary to acidify the samples and to remove IC by sparging a pretreatment gas. To this end, the operator manually acidifies all samples and arranges the same on a sample table, so that the ventilation pretreatment needle sparges the pretreatment gas into all samples.

In another type of a TOC analyzer, samples are first introduced into the TOC analyzer, and thereafter subjected to acidification and sparging one by one for NPOC measurement.

When the sampling needle and the ventilation pretreatment needle are individually driven by different mechanisms, the overall structure is complicated.

While the apparatus for entirely sampling previously acidified samples is suitable for NPOC measurement, on the other hand, application of such an apparatus is restricted since this apparatus cannot carry out measurement of other modes such as TC measurement and IC measurement.

In the apparatus for performing acidification and sampling after the samples are introduced into the TOC analyzer, the overall measuring time is increased.

SUMMARY OF THE INVENTION

An object of the present invention is to provide a sample introducer having a simplified mechanism as well as a high degree of freedom for introducing samples, which can also perform pretreatment of samples.

The inventive sample introducer comprises a sample table which is provided with a plurality of sample containers for moving the sample containers to a prescribed position, a washing port, an arm mechanism holding a sampling needle and a ventilation pretreatment needle for sparging a gas containing no carbon component with a constant distance for inserting the needles into the sample containers or the linsing (i.e. washing) port, and a sample supply mechanism for sucking solutions contained in the sample containers through the sampling needle and supplying the same to an analyzer or other sample containers.

The space between the two needles are so set that the needles are simultaneously inserted in large sample containers while the same are individually inserted in small sample containers.

The sampling needle and the ventilation pretreatment needle are mounted on the same arm mechanism to be driven at the same time, whereby the structure is simplified.

When the two needles are inserted in the same sample container, it is possible to sparge a pretreatment gas such as nitrogen or high-purity air into the sample through the ventilation pretreatment needle to homogenize the sample, or perform sparging for NPOC measurement while sucking the sample with the sampling needle for NPOC measurement, to introduce the sample into an analyzer. When the two needles are inserted in different sample containers, on the other hand, the sampling needle samples the sample for analyzing the same, while the ventilation pretreatment needle is inserted in a sample container which is located in a position for next sampling, to complete ventilation pretreatment in parallel with the analyzing operation.

One of the sample containers contains acid so that the sampling needle sucks the acid and distributively injects prescribed amounts of the acid into other sample containers, so that only samples to be subjected to NPOC measurement can be acidified.

In a preferred example of the sample table employed in the inventive automatic sample introducer, an ultrasonic vibrator is provided in a specific position of a liquid vessel so that a turntable having a plurality of sample containers moves the sample containers in a state dipped in the liquid vessel, while the moving table is provided with reflecting walls which divide the liquid vessel into regions each containing at least one sample container.

The specific position of the liquid vessel provided with the ultrasonic vibrator is a sampling position for sucking samples and introducing the same into an analyzer, or a position immediately ahead thereof, for example.

The sample containers provided on the moving table are moved by the moving table in a state dipped in the liquid vessel, to be located at the sampling position. Liquid samples contained in the sample containers are vibrated by the ultrasonic vibrator, which is provided on the liquid vessel, at the sampling position or the position immediately ahead thereof, to be homogenized. Since the liquid vessel is divided into a plurality of regions by the reflecting walls, vibration of the ultrasonic vibrator is intensively propagated to the sample contained in the region provided with the ultrasonic vibrator.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
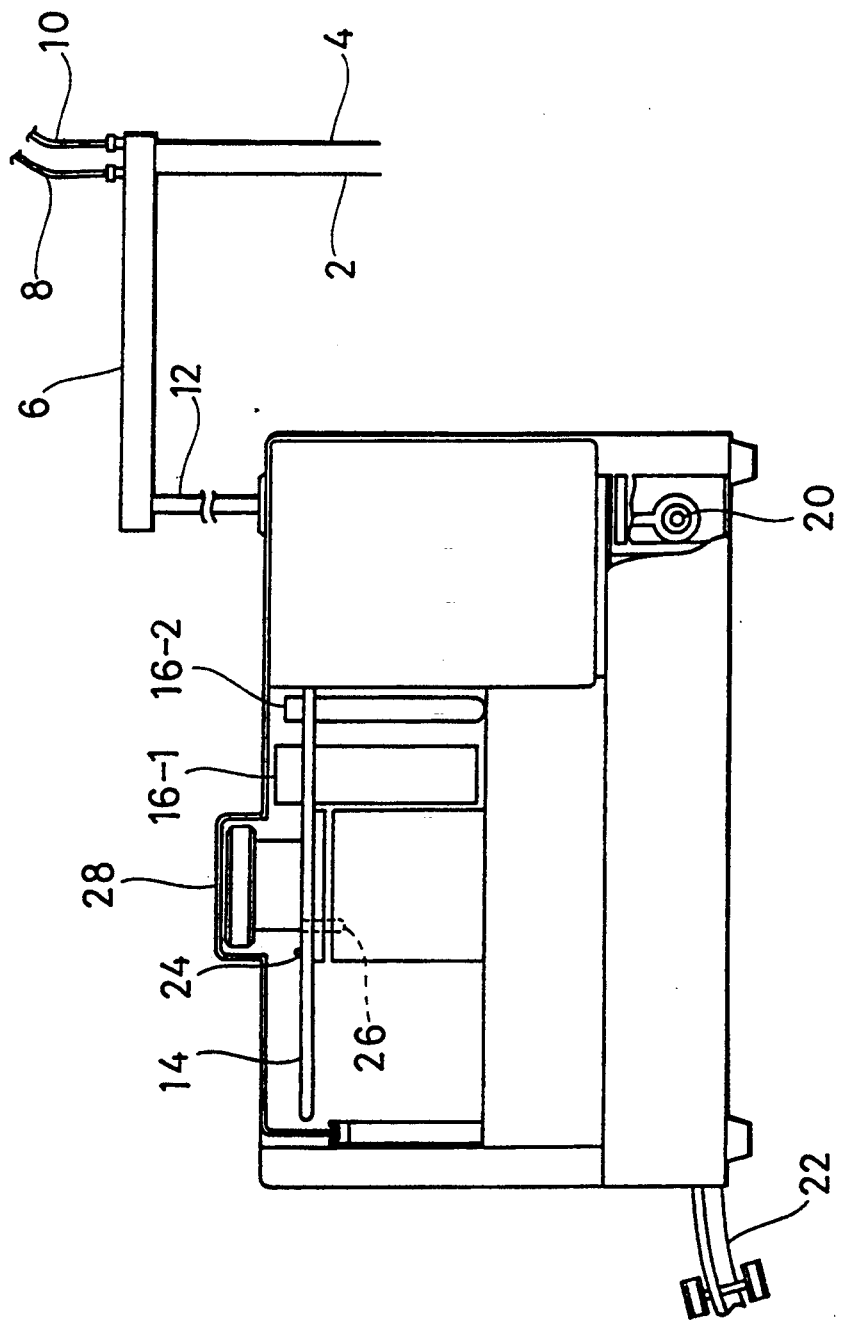
FIG. 1 is a front sectional view showing an embodiment of the present invention.
Figure 2:
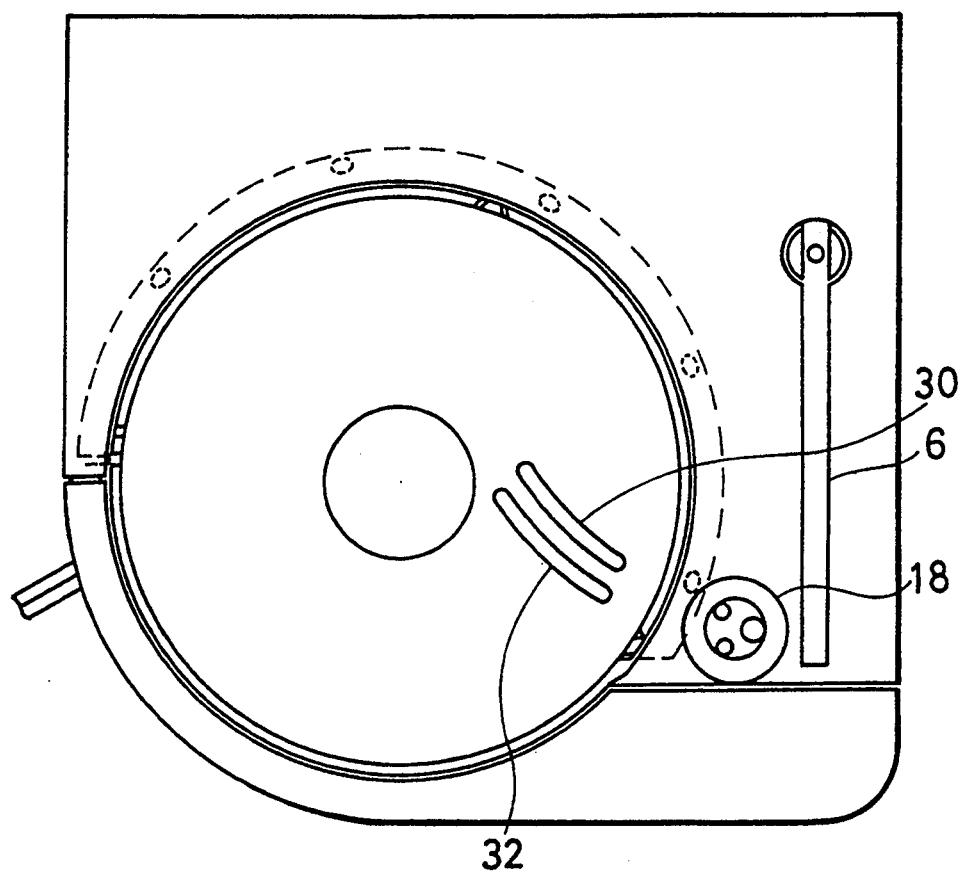
FIG. 2 is a top plan .view showing the embodiment.
Figure 3:
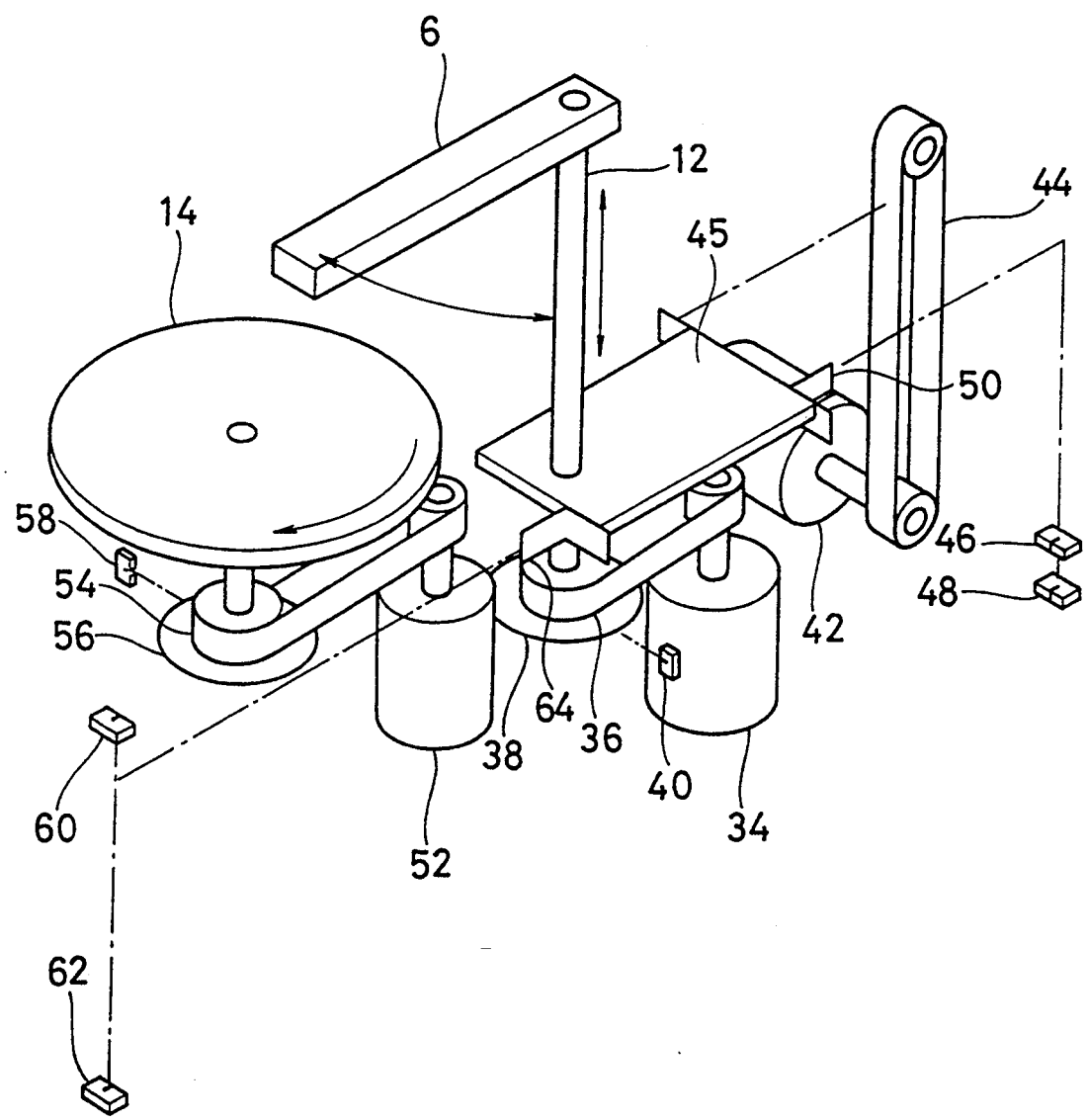
FIG. 3 is an exploded perspective view showing the outline of a mechanism of the embodiment.

FIG. 1 is a front sectional view showing an embodiment of the present invention, FIG. 2 is a top plan view showing the embodiment, and FIG. 3 is a schematic perspective view showing a mechanism part of the embodiment.

Referring to FIG. 1, a sampling needle 2 and a ventilation pretreatment needle 4 are mounted on an end of an arm 6 with a constant space. The needle 2 is introduced to an analyzer through a sampling tube 8. On the other hand, the needle 4 is connected to a mechanism for supplying high-purity air through a sparging tube 10. Another end portion of the arm 6 is mounted on an arm shaft 12, which is so rotated or vertically displaced that the needles 2 and 4 can be inserted in vials 16-1 and 16-2, i.e., sample containers which are mounted on a turntable 14 serving as a sample table, or into a needle linsing port 18 (FIG. 2). Wash water is fed to the linsing port 18 from a linsing pump 20, and then discharged from a drain tube 22.

A plurality of types of turntables 14 are prepared in response to the types of the vials which are mounted thereon, and each turntable 14 is provided with a marker 24 for indicating its type. A locating pin 26 is provided in order to locate the turntable 14 for mounting the same to the body.

The turntable 14 is provided on its upper portion with a cover 28, which also serves as a stopper for preventing upward movement of the vials 16-1 and 16-2, receiving the needles 2 and 4, when the needles 2 and 4 are upwardly moved. As shown in FIG. 2, the cover 28 is provided with flat oval shaped slits 30 and 32 for receiving the needles 2 and 4 respectively, so that the needles 2 and 4 are vertically moved through the slits 30 and 32. The slits 30 and 32 are formed in elliptic configurations in correspondence to operating loci of the needles 2 and 4, which are driven by the arm 6.

FIG. 3 shows a mechanism for driving rotation and vertical movement of the arm 6, and another mechanism for rotating the turntable 14.

An arm rotating motor 34 is provided in order to rotate the arm 6, such that rotation of the motor 34 is transmitted to the arm shaft 12 through a belt 36. The shaft 12 is provided with a rotational position indicating disk 38 for indicating the rotational position of the arm 6, while a photosensor 40 is provided to be combined with this disk 38. The disk 38 has a slit, which is detected by the photosensor 40 for detecting the origin of the rotational position of the arm 6, thereby indicating the rotational position.

An arm driving motor 42 is provided in order to drive the vertical movement of the arm 6, such that rotation of this motor 42 is transmitted to a shaft support plate 45 through a belt 44, to vertically drive the arm shaft 12. Photosensors 46 and 48 are provided on upper and lower positions respectively, in order to detect the vertical position of the arm 6. The photosensor 46 is adapted to detect a home position for driving the arm 6, and the other photosensor 48 is adapted to indicate a position for stopping downward movement of the arm 6. A light shielding plate 50 is mounted on the shaft support plate 45, in order to indicate the arm driving position in combination with the photosensors 46 and 48. An upper limit photosensor 60 and a lower limit photosensor 62 are provided in order to detect upper and lower limits for the vertical movement of the arm 6, while the shaft support plate 45 is provided with a light shielding plate 64 to be combined with the photosensors 60 and 62.

A motor 52 is provided in order to rotate the turntable 14, such that rotation of the motor 52 is transmitted to the turntable 14 through a belt 54. The turntable 14 is provided on its rotary shaft with a disk 56 for detecting the rotational position of the turntable 14, and a photosensor 58 is combined with the disk 56. The disk 56 has a slit, so that the origin of rotation of the turntable 14 is detected by the position of this slit.

Figure 4:
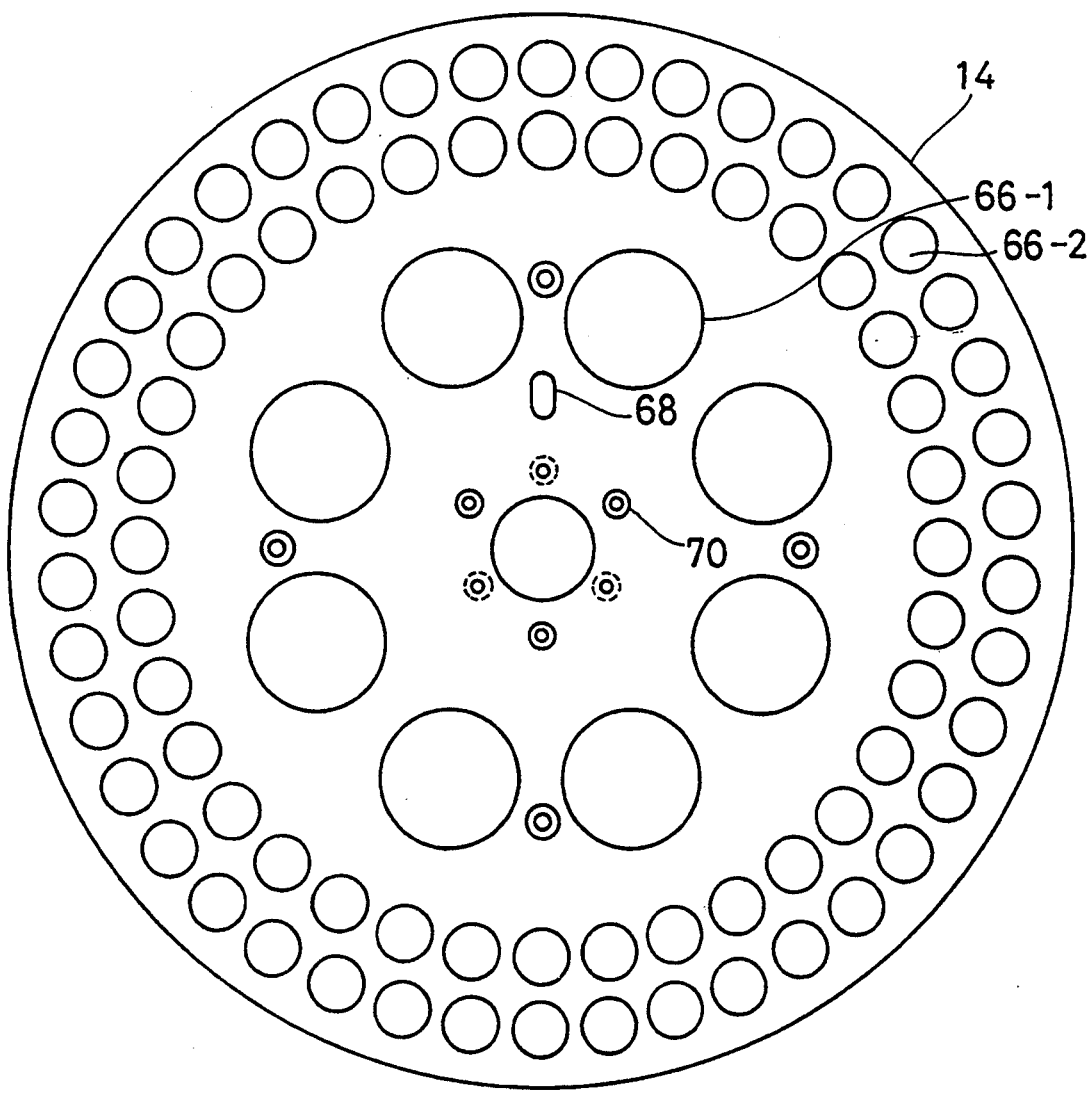
FIGS. 4 and 5 are plan views showing examples of a turntable which is provided in the embodiment.

FIG. 4 shows an example of the turntable 14.

This turntable 14 is provided with holes 66-1 for receiving large sample containers and holes 66-2 for receiving small sample containers. The needles 2 and 4 are simultaneously inserted into each of the large sample containers. As to the small sample containers, on the other hand, the needle 2 is inserted into one of each adjacent pair of containers, while the needle 4 is inserted into the other one.

A hole 68 is adapted to receive the locating pin 26 for locating the turntable 14 on the body, and screwholes 70 are adapted to fix the turntable 14 to the body. The marker 24 indicating the type of the turntable 14 is provided in one of the screwholes 70.

The large sample containers are suitable for low concentration TOC measurement of not more than 1 p.p.m. If ventilation pretreatment is stopped in this case, $CO_2$ contained in the atmosphere dissolves in the samples to increase TOC values. Thus, it is necessary to continue ventilation pretreatment until the samples are completely sampled by the needle 2.

On the other hand, the small sample containers are applied to relatively high density measurement of at least several p.p.m. In this case, ventilation pretreatment is stopped and $CO_2$ dissolves in the samples, while the amounts of the dissolving $CO_2$ exert substantially no influence on the sample measuring values. In order to improve efficiency of measurement, it is better to perform ventilation pretreatment of unmeasured samples during sample measurement, as compared with a case of performing ventilation pretreatment and sample measurement in a serial manner. To this end, it is better to individually insert the needles 2 and 4 into an adjacent pair of the sample containers respectively.

Figure 5:
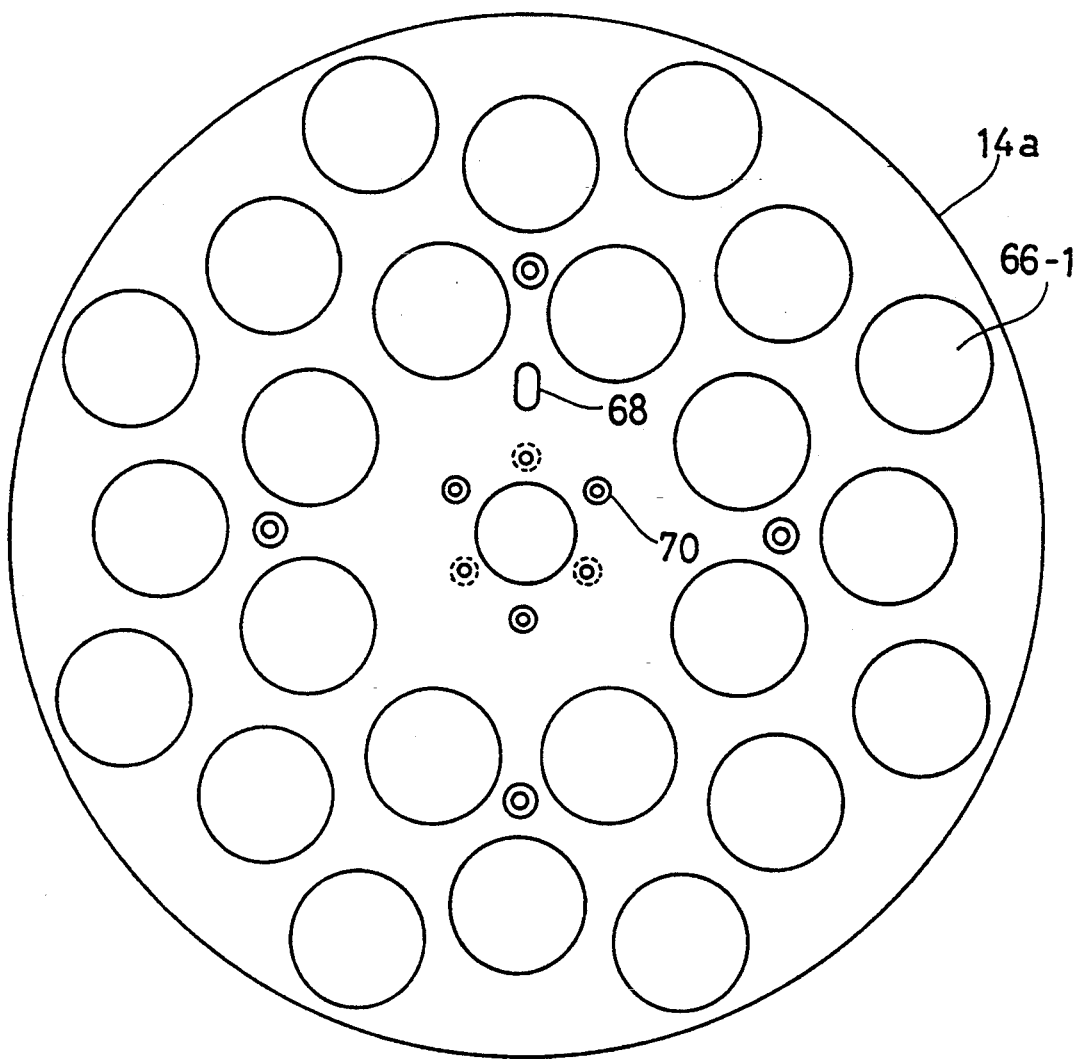

FIG. 5 shows another example 14a of the turntable.

This turntable 14a has only holes 66-1 for receiving large sample containers.

Alternatively, such a turntable may be provided with only holes for receiving small sample containers, each of which is adapted to receive only one needle.

Figure 6:
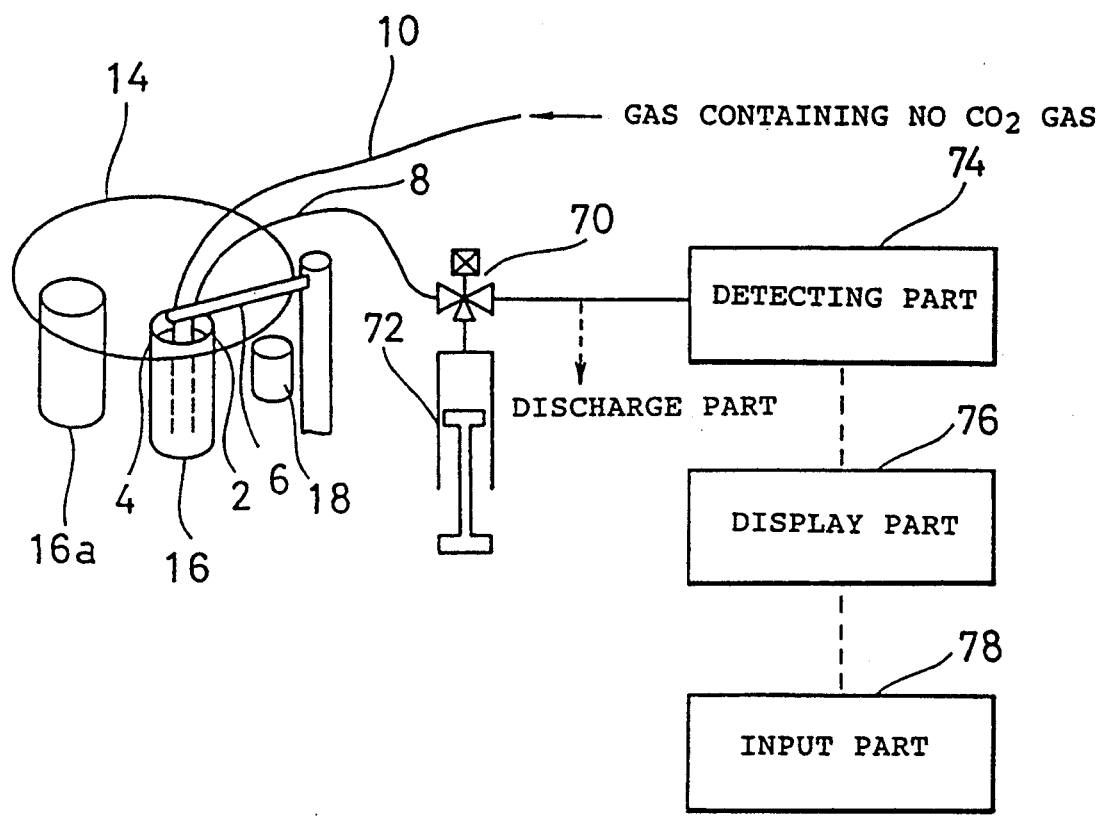
FIG. 6 is a schematic block diagram showing an exemplary TOC analyzer, to which the embodiment is applied.

FIG. 6 shows a TOC analyzer, to which the sample introducer according to the embodiment is applied.

A vial 16a containing acid is set in a specific position of a turntable 14. Other vials 16 contain samples. A needle 2 is connected to a sample injector 72 or a detecting part 74 through a sampling tube 8 and a switching port 70. The sample injector 72 sucks a constant amount of each sample and injects the same into the detecting part 74, or sucks the acid from the vial 16 and injects the same into each vial 16 by a constant amount. A passage between the switching port 70 and the detecting part 74 is provided with a discharge part, which is employed in linsing. A display part 76 displays measurement conditions, measurement situations, measurement data and the like. This TOC analyzer is also provided with a setting part (not shown) for setting the measurement conditions, and a computer control part (not shown) for controlling operations such as pretreatment of the samples, injection of the samples, measurement and the like, as well as processing the measurement data.

In order to perform NPOC measurement, it is necessary to acidify the samples. As to each sample for which NPOC measurement is specified, therefore, the acid contained in the vial 16a is distributively injected through the sample injector 72 by an amount set at the measurement condition setting part in advance of measurement. As to such distributive injection of the acid, the sample injector 72 and a related passage are washed and substituted with the acid by a set number of times. Then the necessary total amount of the acid is evaluated from the set number of the samples to be supplied with the acid and the amount of acid injection for distributive injection of the acid. The sample injecter 72 sucks the acid by at least the evaluated total amount, so that the acid is distributively injected into the sample vials 16. If single suction is insufficient, the acid is sucked by a required number of times, to be distributively injected into the vials 16.

On the other hand, the needle 4 ventilates the samples with a gas substantially containing no $CO_2$ gas for a period which is set under the measurement conditions.

The needle 2 is inserted in the linsing port 18, which contains or passes wash water, upon injection of the acid into each sample, so that its surface is washed. After the acid is distributively injected into all samples, the wash water contained in the linsing port 18 is sucked by the sample injector 72 and discharged to the discharging part, to wash the sample injector 72 and the related passage. Further, the wash water contained in the linsing port 18 is sucked by the sample injector 72 by a prescribed number of times every sample measurement or after overall sample measurement, and discharged to the discharge part to wash the sample injector 72 and the related passage.

An exemplary operation of the TOC analyzer shown in FIG. 6 is now described.

The vial 16a containing the acid is set in the prescribed position of the turntable 14, and the measurement conditions are set. As to the sample vials 16, for example, those numbered 1 to 6 are set for TC measurement while those numbered 7 to 12 are set for NPOC measurement. Further, automatic addition of the acid is indicated and the amount of the added acid is set at 50 $\mu l$, for example.

Upon starting of the measurement, the needle 2 is first inserted in the vial 16a containing the acid, and the switching port 70 is switched to the needle 2 side so that the sample injector 72 sucks the acid. Then the switching port 70 is switched to the detecting part 74 side, so that the sucked acid is discharged to the discharge part. This operation is repeated a plurality of times, so that the passage between the needle 2 and the sample injector 72 as well as the sample injector 72 are washed with the acid. Then the acid is sucked and injected. Assuming that the capacity of the sample injector 72 employed in this embodiment is 250 $\mu l$, for example, the acid is first sucked by 50 $\mu l \times 5 = 250$ $\mu l$, so that the needle 2 distributively injects the acid by 50 $\mu l$ into every one of the sample vials 16 numbered 7 to 11, for which NPOC measurement is specified. If specification is previously given, the needle 2 is moved to the linsing port 18 upon every distributive injection of the acid, so that its surface is washed. Then the needle 2 is again moved to the acid vial 16a to suck the acid by 50 $\mu l$, to inject the same to the 12th sample vial 16. Thereafter the needle 2 is moved to the linsing port 18 to suck the wash water contained in the linsing port 18 and discharge the same several numbers of times through the sample injector 72, so that the same is washed. Then the needle 2 is moved to the first sample vial 16 and washed by the sample injector 72 with the sample, which in turn is measured and sucked to be injected into the detecting part 74. In the case of NPOC measurement, the ventilation pretreatment needle 4 feeds the gas containing no $CO_2$ gas for a certain period for ventilation, and thereafter the sample is measured from the sampling needle 2 by the sample injector 72, to be injected into the detecting part 74. The wash water contained in the linsing port 18 is sucked and discharged every sample measurement or after overall sample measurement for linsing.

Thus, one of the sample containers contain the acid so that the acid is sucked by the sampling needle and distributively injected into the remaining sample containers by prescribed amounts, whereby the acid can be automatically added to the samples for NPOC measurement and the samples can be automatically ventilated on the sample table in advance of measurement, and hence the overall measurement time is reduced. Comparing this structure with the conventional case of acidifying and ventilating samples which are introduced into the TOC analyzer, the measurement time, which has generally taken about 8 minutes as to every sample, is reduced to about 3 minutes, whereby the time required for addition of acid and ventilation is reduced by about 5 minutes. Comparing the present invention with the conventional apparatus of arranging previously acidified samples on a sample table, further, the acid adding step is automated for labor-saving.

Since the samples to be acidified can be previously set, it is possible to arrange the samples requiring acidification for NPOC measurement and those requiring no acidification for TC or IC measurement on the same sample table.

Since the sample injector also serves as an acid injector, the cost is reduced and the injection amount can be correctly set in units of several $\mu l$.

Since it is possible to wash the acid injection tube, no contamination is caused between the samples during distributive injection of the acid.

Since all passages between the sample injecting needle and the sample injector can be washed every sample measurement or after overall sample measurement, it is possible to prevent corrosion and clogging which may be caused by the samples, even if the samples contain acid or salt.

Figure 7:
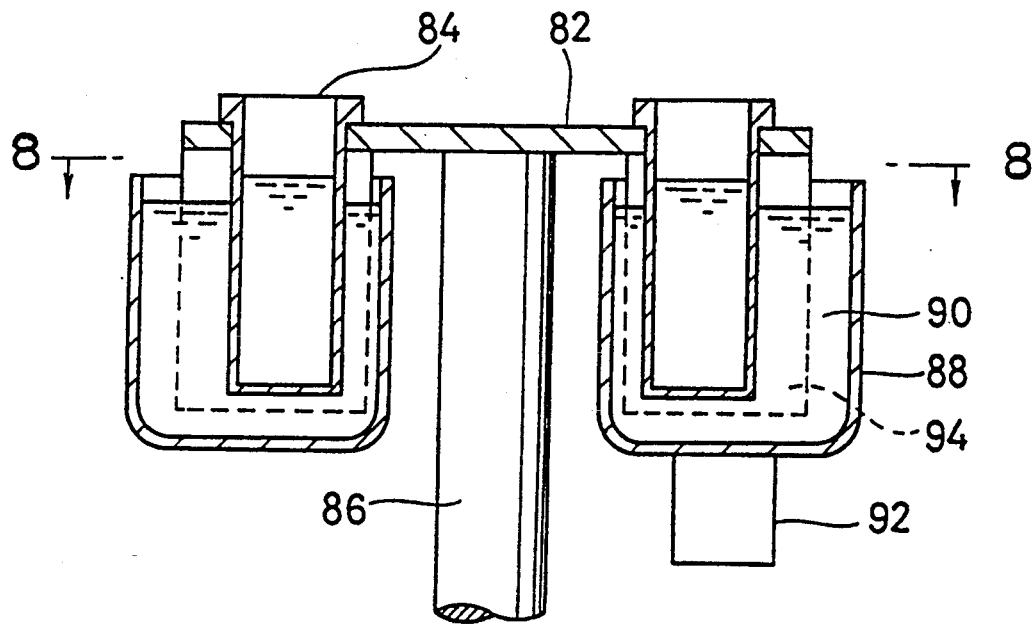
FIG. 7 is a longitudinal sectional view taken along the line 7—7 in FIG. 8 for showing a preferable sample table.
Figure 8:
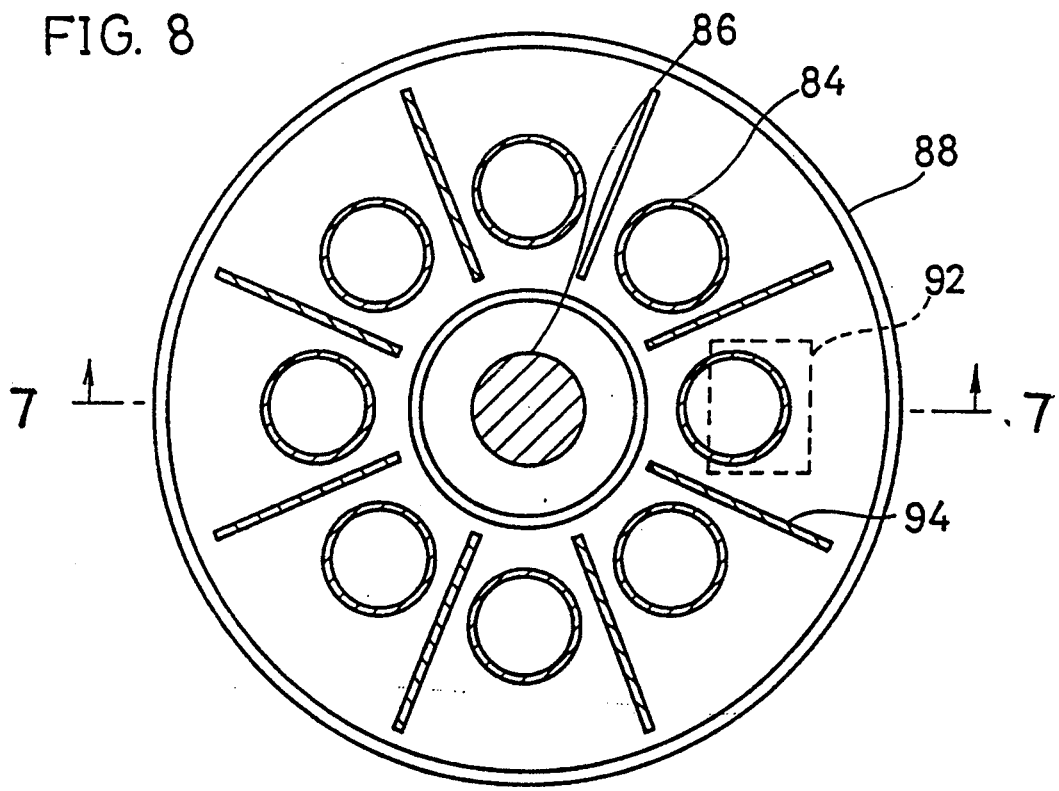
FIG. 8 is a sectional view taken along the line 8—8 in FIG. 7.

If nitrogen or the like is merely sparged and mixed into the sample containers before sampling, it is not possible to attain sufficient ability for refining suspended matters (homogenizability). FIGS. 7 and 8 illustrate a sample table comprising means which can mix liquid samples, contained in sample containers, so that the samples are sufficiently refined before being sucked by the sample introducer. FIG. 7 is a vertical sectional view, and FIG. 8 is a sectional view taken along the line A—A in FIG. 7.

A turntable 82, serving as a moving table, has a plurality of sample receiving holes along its circumference, so that sample containers 84 are inserted in the holes.

The turntable 82 is rotated about its rotary axis 86, to locate samples to be introduced into an analyzer, such as a TOC analyzer, in a sampling position.

A liquid vessel 88 is provided in order to vibrate every sample container 84. This liquid vessel 88 contains water 90, for example, so that each sample container 84 mounted on the turntable 82 is dipped in the water 90, which is contained in the liquid vessel 88, and moved. An ultrasonic vibrator 92 is mounted on a lower surface of a specific position, such as the sampling position or next sampling position, for example, of the liquid vessel 88.

Reflecting walls 94 are mounted on the turntable 82 in order to divide the interior of the liquid vessel 88 into a plurality of regions. These reflecting walls 94 are so provided that each of the spaces defined by the same receives one sample container 84. The reflecting walls 94 may have sufficient reflectance with respect to ultrasonic waves, while the same preferably have corrosion resistance, in consideration of employment in the liquid. Such reflecting walls 94 are formed by stainless steel plates, for example.

The operation of this sample table is now described.

The turntable 82, the sample containers 84 mounted on the turntable 82, and the reflecting walls 94 are rotated upon rotation of the rotary shaft 86 which is driven by a power source (not shown), so that the sample container 84 containing the sample to be introduced into the analyzer is located at the sampling position. The liquid vessel 88 and the ultrasonic vibrator 92 are fixed, while the sample container 84 located at the sampling position is vibrated by the ultrasonic vibrator 92 so that the liquid sample contained in the sample container 84 is homogenized by such vibration.

Even if no reflecting walls 94 are provided, the ultrasonic waves are considerably attenuated in a position separated from the vibrator 92 in a cavitation region of the liquid vessel 88. As a matter of course, the sample reaches the cavitation region in the liquid vessel 88 to be homogenized. However, the liquid vessel 88 is divided into the plurality of regions by the reflecting walls 94, to improve power efficiency of the liquid vessel region provided with the ultrasonic vibrator 92.

While the liquid vessel 88 is so divided by the reflecting walls 94 that each of the divided regions receive one sample container 84, the divided regions may alternatively be set so that each region receive two or more sample containers.

In this sample table, the ultrasonic vibrator is provided in a specific position of the liquid vessel so that the sample containers are moved in a state dipped in the liquid vessel while the liquid vessel is divided into a plurality of regions by the reflecting walls, whereby it is possible to effectively homogenize the samples while improving power efficiency of the ultrasonic vibrator.

Since the sample containers are dipped in the liquid vessel in this sample table, it is possible to use the liquid vessel for homogenization also as a constant-temperature bath, by adjusting the liquid temperature in the liquid vessel.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A sample introducer, comprising:
   a support;
   a sample table accommodated on said support, said sample table capable of accommodating a plurality of sample containers and moving said sample containers to a prescribed sampling position, said sample table capable of accommodating both sample containers having dimensions for simultaneously receiving both a sampling needle and a ventilation pretreatment needle, and sample containers having dimensions for receiving only one of the needles;
   a washing port accommodated on said support;
   an arm mechanism accommodated on said support;
   a sampling needle supported for movement by said arm mechanism;
   a ventilation pretreatment needle supported for movement on said arm mechanism for sparging the sample containers, said arm mechanism provided for inserting the needles into said sample containers provided on said sample table and, alternatively, said washing port, and for moving said needles back and forth between said sampling position and said washing port;
   a sparging gas supply fluidly connected to said ventilation pretreatment needle; and
   a sample supply mechanism for withdrawing liquids from said sample containers through said sampling needle by suction and supplying said liquids to other equipment.

2. A sample introducer in accordance with claim 1, wherein said needles are arranged so that said ventilation pretreatment needle is inserted in a sample container located at a position for next sampling when said sampling needle is inserted in a sample container located at said sampling position.

3. A sample introducer in accordance with claim 1, wherein said sample table is configured for only accommodating sample containers having dimensions for simultaneously receiving both said needles.

4. A sample introducer in accordance with claim 1, wherein said sample table is configured for only accommodating sample containers having dimensions for receiving only one of said needles, and both said needles are arranged so that said ventilation pretreatment needle is inserted in a sample container located at a next sampling position when said sampling needle is inserted in a sample container located at said sampling position.

5. A sample introducer, comprising:
   a support;
   a liquid vessel accommodated on the support, said liquid vessel having an ultrasonic vibrator in a specific position;
   a sample table accommodated on said support, said sample table configured for accommodating a plurality of sample containers and for dipping and moving said sample containers in said liquid vessel;
   reflecting walls mounted on said sample table for dividing said liquid vessel into a plurality of regions each having dimensions for accommodating at least one said sample container;
   a linsing port accommodated on said support;
   an arm mechanism accommodated on said support;
   a sampling needle supported for movement by said arm mechanism;
   a ventilation pretreatment needle supported for movement by said arm mechanism for sparging the sample containers, said arm mechanism provided for inserting the needles into said sample containers provided on said sample table and, alternatively, said linsing port, and for moving said needles back and forth between said sampling position and said linsing port;

a sparging gas supply fluidly connected to said ventilation pretreatment needle; and a sample supply mechanism for withdrawing liquids from said sample containers through said sampling needle by suction and supplying said liquids to other equipment.

6. A sample introducer in accordance with claim 5, wherein each of said regions divided by said reflecting walls has dimensions for accommodating only one of said sample containers.

7. A sample introducer in accordance with claim 5, wherein said ultrasonic vibrator is arranged at said sampling position.

8. A sample introducer in accordance with claim 5, wherein said liquid vessel is a constant-temperature bath.

9. A sample introducer in accordance with claim 5, wherein said ultrasonic vibrator is arranged at a position immediately ahead of said sampling position.

10. A sample introducer, comprising:
a support;
a sample table accommodated on said support, said sample table capable of accommodating a plurality of sample containers and move the sample containers to a prescribed sampling position;
a washing port accommodated on aid support;
an actuating arm accommodated on said support;
a sampling needle for sampling the sample containers, said sampling needle supported for movement by said actuating arm;
a ventilation pretreatment needle for sparging the sample containers, said ventilation pretreatment needle supported for movement on said actuating arm;
a sparging gas supply fluidly connected to said ventilation pretreatment needle;
a mechanism accommodated on said support for manipulating said actuating arm for inserting the needles into said sample containers provided on said sample table and, alternatively, said washing port, and for moving said needles back and forth between said sampling position and said washing port; and
a sample supply mechanism for withdrawing liquids from said sample containers through said sampling needle by suction and supplying said liquids to other equipment.

11. A sample introducer according to claim 10, wherein said sample table is rotatably mounted on said support, and said actuating arm is a pivoting arm having a fixed length for moving said needles back and forth between said sampling position and said linsing port.

12. A sample introducer according to claim 11, wherein both said needles are supported at one end of said pivoting arm.

13. A sample introducer according to claim 12, wherein said needles are positioned parallel and side-by-side.

14. A sample introducer, comprising:
a support;
a sample table supported for movement on said support, said sample table configured for accommodating sample containers and for moving the sample containers to a sampling position;
a linsing port accommodated on said support;
an arm mechanism supported for movement on said support;
a sampling needle for sampling the sample containers, said sampling needle supported for movement on said arm mechanism;
a sparging needle for supplying sparging gas to the sample containers, said sparging needle supported for movement on said arm mechanism, and said sparging needle positioned adjacent said sampling needle and moved together by said arm mechanism between said sampling position and said linsing port;
a sparging gas supply fluidly connected to said ventilation pretreatment needle; and
a sample supply mechanism for withdrawing liquids from said sample containers through said sampling needle by suction and supplying said liquids to other equipment.

15. A sample introducer according to claim 14, wherein said arm mechanism includes a pivoting arm mounted on said support and supporting the needles, said arm mechanism also including an actuating mechanism for moving said pivoting arm so that said needles move between said sampling position and said linsing port.

16. A sample introducer according to claim 15, wherein said actuating mechanism moves said pivoting arm upwardly and downwardly to accomplish sampling and linsing operations.

17. A sample introducer according to claim 15, wherein said pivoting arm has a fixed length, and supports said needles at one end thereof.

* * * * *